United States Patent
Jha et al.

(10) Patent No.: US 9,846,112 B2
(45) Date of Patent: Dec. 19, 2017

(54) EXTERIOR AIRCRAFT LIGHTING DEVICE

(71) Applicant: Goodrich Lighting Systems GmbH, Lippstadt (DE)

(72) Inventors: Anil Kumar Jha, Lippstadt (DE); Andre Hessling-Von Heimendahl, Koblenz (DE); Christian Schoen, Mainz (DE)

(73) Assignee: GOODRICH LIGHTING SYSTEMS GMBH, Lippstadt (DE)

( * ) Notice: Subject to any disclaimer, the term of this patent is extended or adjusted under 35 U.S.C. 154(b) by 22 days.

(21) Appl. No.: 15/159,047

(22) Filed: May 19, 2016

(65) Prior Publication Data

US 2016/0341655 A1 Nov. 24, 2016

(30) Foreign Application Priority Data

May 20, 2015 (EP) .................................... 15168383

(51) Int. Cl.

| | |
|---|---|
| *G01N 21/00* | (2006.01) |
| *G01N 17/00* | (2006.01) |
| *B64D 47/02* | (2006.01) |
| *F21V 5/04* | (2006.01) |
| *H05B 37/02* | (2006.01) |
| *H05B 33/08* | (2006.01) |

(52) U.S. Cl.
CPC ........... *G01N 17/004* (2013.01); *B64D 47/02* (2013.01); *F21V 5/045* (2013.01); *H05B 33/0893* (2013.01); *H05B 37/0218* (2013.01)

(58) Field of Classification Search
CPC ...... G01N 17/004; B64D 47/02; F21V 5/045; H05B 33/0893; H05B 37/0218

USPC .......................................................... 356/72
See application file for complete search history.

(56) References Cited

U.S. PATENT DOCUMENTS

| | | |
|---|---|---|
| 7,414,546 B2 | 8/2008 | Singer et al. |
| 8,773,044 B2 | 7/2014 | Hessling |
| 8,974,097 B2 | 3/2015 | Hessling et al. |

(Continued)

FOREIGN PATENT DOCUMENTS

| | | |
|---|---|---|
| EP | 1126430 A2 | 8/2001 |
| EP | 1240458 A2 | 9/2002 |

(Continued)

OTHER PUBLICATIONS

Extended European Search Report of the European Patent Office for International Application No. EP15168383.6, dated Oct. 21, 2015, 4 pages.

*Primary Examiner* — Hina F Ayub
(74) *Attorney, Agent, or Firm* — Cantor Colburn LLP

(57) ABSTRACT

An exterior aircraft lighting device comprises: at least one light source; an optical element having a light entry side facing the at least one light source and a light exit side and being configured for modifying light emitted by the at least one light source; at least one photo detector, which is configured and arranged for detecting a portion of the light emitted by the at least one light source, which is reflected by the light entry side of the at least one optical element, the photo detector providing a detection value, representing the amount of detected light; and a control and evaluation unit which is configured for evaluating the state of wear of the at least one light source based on the detection value provided by the at least one photo detector.

15 Claims, 2 Drawing Sheets

(56) References Cited

U.S. PATENT DOCUMENTS

| | | | |
|---|---|---|---|
| 2003/0001119 A1* | 1/2003 | Takezawa | G01N 21/952 250/559.45 |
| 2007/0177144 A1* | 8/2007 | Hasegawa | G01J 3/02 356/328 |
| 2009/0050827 A1* | 2/2009 | Takahashi | F16C 19/386 250/577 |
| 2013/0300296 A1 | 11/2013 | Mueller | |
| 2015/0262491 A1* | 9/2015 | Seelamonthula | G08G 5/025 340/953 |

FOREIGN PATENT DOCUMENTS

| | | |
|---|---|---|
| JP | 2003067967 A | 3/2003 |
| KR | 100294886 B1 | 4/2001 |
| WO | 2013140280 A2 | 9/2013 |

* cited by examiner

EXTERIOR AIRCRAFT LIGHTING DEVICE

FOREIGN PRIORITY

This application claims priority to European Patent Application No. 15 168 383.6 filed May 20, 2015, the entire contents of which is incorporated herein by reference.

TECHNICAL FIELD

The present invention relates to an exterior aircraft lighting device comprising at least one light source, in particular to an exterior aircraft lighting device allowing near end of life detection of the least one light source.

BACKGROUND OF THE INVENTION

Almost all aircraft are equipped with exterior lights. In particular, large passenger air planes have a wide variety of exterior lights. Examples are navigation lights or position lights, beacon lights, anti-collision lights or strobe lights, wing lights, taxi lights, landing lights, runway turnoff lights, etc. These lights are provided with at least one light source having a limited life span. For safety reasons, every light source has to be replaced before the end of its lifespan has been reached.

It therefore would be beneficial to provide an exterior aircraft lighting device allowing near end of life detection (NEOL-detection) for determining an optimized point in time for changing the respective light source. In case an aircraft lighting device comprises a plurality of light sources, it would in particular be beneficial to allow individual NEOL-detection for every light source without much additional effort.

SUMMARY

Exemplary embodiments of the invention include an exterior aircraft lighting device comprising: at least one light source; an optical element having a light entry side facing the at least one light source and an opposing light exit side, the optical element being configured for modifying the light emitted by the at least one light source; at least one photo detector, and a control and evaluation unit. The at least one photo detector is configured and arranged for detecting a portion of the light emitted by the at least one light source and reflected by the light entry side of the at least one optical element. The at least one photo detector is further configured for providing at least one detection value representing the amount of detected light. The control and evaluation unit is configured for evaluating the state of wear of the at least one light source based on the at least one detection value provided by the at least one photo detector.

The term "reflected" as it is used in the context of the present application includes direct light reflection as well as diffuse light reflection which is caused by light being scattered at the light entry side of the optical element.

A method of evaluating the state of wear of at least one light source of an exterior aircraft lighting device comprises the steps of: operating the at least one light source for irradiating light onto a light entry side of at least one optical element configured for focussing light, which has entered through the light entry side, and emitting the focused light through a light exit side; detecting a portion of light emitted by the at least one light source, which has been reflected by the light entry side of at least one optical element; providing a detection value representing the amount of detected light; and evaluating the state of wear of the at least one light source based on the provided detection value.

Detecting and evaluating a portion of light which has been reflected by the optical element provides an easy and reliable way of automatically determining the state of wear of the at least one light source of an exterior aircraft lighting device. Basically, only an additional photo detector and an electronic evaluation circuit need to be provided. Monitoring the at least one light source of an exterior aircraft lighting device allows to replace the at least one light source when necessary. It in particular avoids an unnecessary replacement of the at least one light source when it works still fine. This reduces the maintenance costs and grounding times of the aircraft. Uncertainties caused by human factors are avoided, and flight safety is enhanced.

The light emitted by the at least one light source is intended to leave the light exit side of the optical element and to contribute to the light output of the exterior aircraft lighting device. The light reflected by the light entry side is a by-product that would be waste light in the absence of the detection use at the photo detector. In other words, the light reflected by the light entry side and detected by the photo detector is part of the useful light of the exterior aircraft lighting device. No light source dedicated to the evaluation of the state of wear of the at least one light source is provided.

In an exemplary embodiment, the at least one light source comprises a plurality of light emitting elements, in particular a row or an array of LEDs providing cheap, efficient and reliable light sources. The photo detector in particular may be arranged in a position which allows to detect light emitted from each of a plurality of light sources/light emitting elements provided in the lighting device. In consequence, a plurality of light sources/light emitting elements may be monitored with a single photo detector. This considerably minimizes the costs for monitoring the light sources/light emitting elements.

In case of a plurality of light sources/light emitting elements are provided, the control and evaluation unit in particular may be configured for successively activating and individually evaluating the plurality of light emitting elements in order to separately evaluate the state of wear of each of the light sources/light emitting elements. This allows to individually replace each of the light sources/light emitting elements, if necessary, and avoids any unnecessary replacement of light sources/light emitting elements which still work properly. Alternatively, this allows to individually control each of the light sources/light emitting elements, in order to adjust for the state of wear. For example, in the case of LEDs being used as light sources, LEDs with higher wear, i.e. LEDs with lower light output due to wear, can be driven with higher drive currents, compensating for the higher wear.

In a further embodiment, the control and evaluation unit comprises a memory unit which is configured for storing at least one reference value. According to an embodiment, the control and evaluation unit is configured for comparing an actual value of a detection signal provided by the photo sensor with said reference value. The reference value in particular may be the value of a previously stored detection signal. The control and evaluation unit may further be configured for issuing a notification signal, when the difference between the reference value and the actual value of the detection signal exceeds a predetermined threshold. In a particular embodiment, a notification signal is triggered, when the actual value of the detection signal is less than 70% of the reference value.

The term actual value of the detection signal refers to a momentary value of the detection signal. The momentary values of the detection signal may be measured in set time intervals, e.g. via a sampling of the detection signal, or as a consequence of certain events, such as a powering up of the exterior aircraft lighting device. In general, a plurality of actual values are taken from the detection signal over time.

By comparing the actual value of the detection signal with the value of a previously stored detection signal, any deterioration of the quality of any of the light sources due to wear can be reliably detected. A previously stored value of a detection signal, which has been generated in combination with a new light source, provides a well suited reference value allowing a reliable detection of the wear of the light source.

In case a plurality of light sources are present, an individual reference value may be present for each light source and a detection value may be provided for each light source, with the state of wear being determined individually for each of the plurality of light sources by comparing the respective detection and reference values. In other words, each of the at least one detection value may be associated with a respective one of the at least one light source.

According to a further embodiment, each of the at least one light source is an LED.

According to a further embodiment, the optical element is a collimating lens.

In a further embodiment, the exterior aircraft lighting device further comprises a temperature sensor which is configured for measuring the temperature within the exterior aircraft lighting device and for providing a corresponding temperature value. In this case, the control and evaluation unit may be configured for taking the temperature value into account when evaluating the state of wear of the at least one light source. As the amount of light emitted by a light source may strongly depend on the actual temperature, taking the actual temperature into account when evaluating the state of wear of the at least one light source avoids false notifications and unnecessary replacements of the light source(s) due to temperature changes.

The control and evaluation unit in particular may be configured for evaluating the state of wear of the at least one light source only when the measured temperature value is within a predetermined temperature range, in particular a temperature range which corresponds to a temperature range for which a reference value is provided in order to avoid a false detection of a malfunction caused by the temperature dependency of the light emission.

Alternatively or additionally, the control and evaluation unit may be configured for adjusting the detection value and/or the reference value based on the measured temperature value in order to compensate for changes of the detection value which are caused by temperature variations. This may also include selecting the reference value, which is compared with the actual value of the detection signal, from a plurality of reference values, wherein each of said reference values is assigned to a different temperature or temperature range.

In a further embodiment, the exterior aircraft lighting device further comprises at least one colorful light emitting element which is operable for correcting chromatic shifts of the light emitted by the at least one light source. This allows to keep the chromatics of the light emitted by the exterior aircraft lighting device within a specified color window (wavelength range) without replacing any light source.

In a further embodiment, the exterior aircraft lighting device further comprises an external cover and a reference light source. In said embodiment, the control and evaluation unit may be configured for determining the state of erosion of the external cover by operating the reference light source for irradiating light onto the external cover; detecting the amount of light, emitted by the reference light source and reflected by the external cover, by the at least one photo detector; and evaluating the state of erosion of the external cover based on the amount of light detected by the at least one photo detector.

An exterior aircraft lighting device according to such an embodiment does not only allow for an automatic NEOL-detection of the at least one light source and/or its light emitting elements, but further allows for automatically determining the amount of erosion of the transparent external cover. This allows to determine when the external cover needs to be replaced due to erosion, considerably reducing the costs for maintenance without deteriorating safety.

In a further embodiment, the exterior aircraft lighting device further comprises an additional optical element arranged between the external cover and at least one of the photo detector and the reference light source. The additional optical element is in particular configured for focusing the light emitted by the additional reference light source onto the external cover and/or for focusing the light reflected by the external cover onto the at least one photo detector.

In a further embodiment, the exterior aircraft lighting device further comprises at least one indicator element, in particular an optical indicator element, which is configured for indicating the need for replacement of at least one of the light emitting elements of the exterior aircraft lighting device. In a particular embodiment, a plurality of indicator elements may be provided. Preferably, each of said plurality of indicator elements is assigned to one of the light emitting elements in order to allow to individually indicate a need for replacement for each of the light emitting elements separately. The optical indicator element(s) may be LED(s).

In a particular embodiment, the at least one indicator element is visible from outside the aircraft when the exterior aircraft lighting device is installed at an aircraft, allowing the pilot as well as service and maintenance personnel to determine the state of the at least one light source and/or the cover easily in the course of outside inspection of the aircraft. Alternatively or additionally, indicator elements may be provided within the aircraft's cockpit for allowing a visual inspection by the cockpit crew.

In an embodiment, the at least partially transparent cover has an arcuate shape, which in particular matches an aircraft's outer contour for optimizing the aerodynamic properties of the lighting device and the aircraft.

In an embodiment, the exterior aircraft lighting device is configured as a navigation or position light, a beacon light, an anti-collision or strobe light, a wing light, a taxi light, a landing light, or a runway turnoff light allowing an easy and fast maintenance of the respective light.

The additional features, modifications, and effects described above with respect to the exterior aircraft lighting device, apply to the method of evaluating the state of wear of an exterior aircraft lighting device in an analogous manner. Analgous method steps are disclosed herewith.

BRIEF DESCRIPTION OF DRAWINGS

Exemplary embodiments of the invention are described in greater detail below with reference to the enclosed figures.

DETAILED DESCRIPTION OF THE INVENTION

Figure 1:
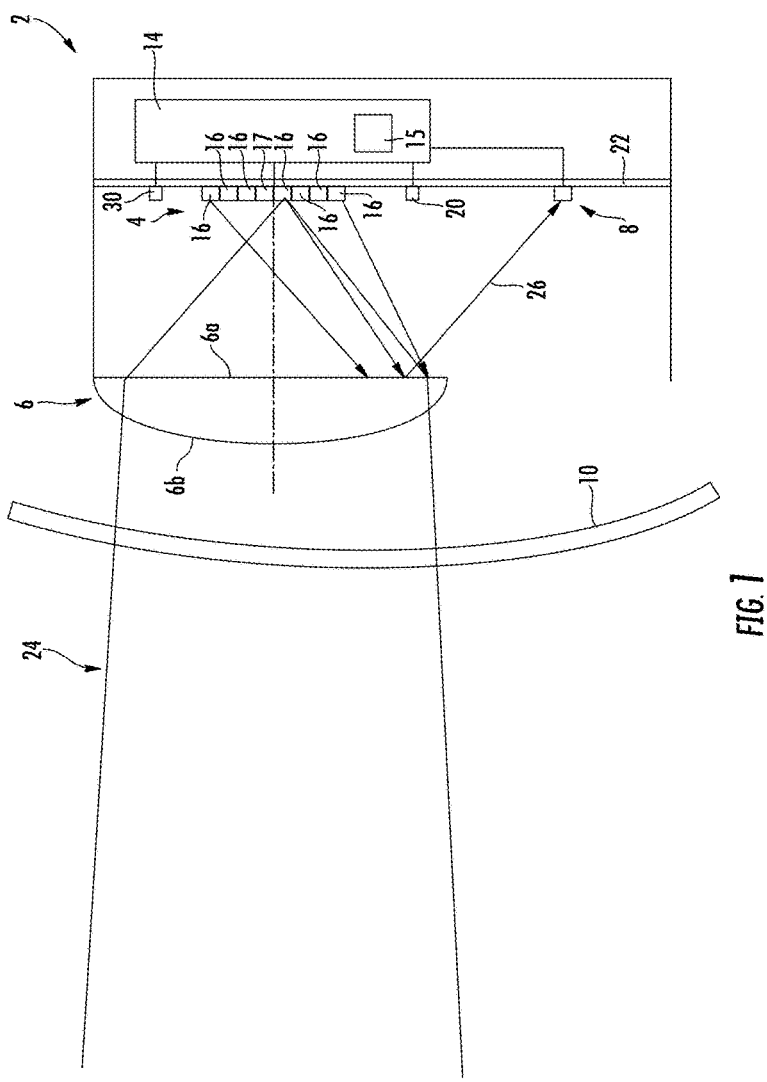
FIG. 1 shows a schematic cross-sectional view of an exterior aircraft lighting device according to an exemplary embodiment of the invention.

FIG. 1 shows a schematic cross-sectional view of an exterior aircraft lighting device 2, which is capable of NEOL-detection, according to an exemplary embodiment of the invention.

The exterior aircraft lighting device 2, according to the exemplary embodiment shown in FIG. 1, comprises a transparent external cover 10 and an opposing structural wall 22 supporting a light source 4. In the exemplary embodiment shown in FIG. 1, the light source 4 is provided as a light source arrangement comprising a plurality of light emitting elements 16, which are arranged next to each other. In an alternative embodiment, which is not shown in the Figures, the light source 4 may comprise only a single light emitting element 16. The light emitting elements 16 in particular may be arranged in a one-dimensional strip, as a two-dimensional array/matrix structure, or in any other pattern which is suitable for generating the desired light emission. The light emitting elements 16 may be embodied as LEDs providing highly efficient light emitting elements 16. Depending on the function of the exterior aircraft lighting device 2, the light emitting elements 16 may be configured for emitting light of the same color, or they may be configured for emitting light of different colors.

An optical element 6 having a light entry side 6a and an opposing light exit side 6b is arranged between the light source 4 and the external cover 10 in a configuration in which light entry side 6a faces the light source 4 and the light exit side 6b faces the external cover 10. The light emitted by the light source 4 enters into the optical element 6 via its light entry side 6a and exits the optical element 6 via its light exit side 6b. The optical element 6 in particular is provided as a focusing element, e.g. a focusing lens, also referred to as a collimating lens, in particular a Fresnel lens, which is configured for focusing the light emitted by the light source 4, generating a focused light beam 24.

The distance between the light source 4 and the light entry side 6a of the optical element 6 typically may be in the range of 5 mm to 50 mm.

For providing an exterior aircraft lighting device 2 operating with high efficiency, the light entry side 6a of the optical element 6 preferably is configured for reflecting as little light as possible. However, a portion 26, typically between 4% to 5% of the light emitted by the light source 4, is still reflected from the light entry side 6a back into the direction towards the structural wall 22. The portion 26 of the light, which is reflected by the light entry side 6a, may be reduced to 1% to 4% by coating the light entry side 6a with an anti-reflecting coating.

A photo detector 8 is provided at said structural wall 22. The photo detector 8 is configured for detecting the reflected portion 26 of the light and for providing a detection signal representative of the amount of light detected by the photo detector 8. The distance between the photo detector 8 and the center of the light source 4 along the extension of the structural wall 22, i.e. in the vertical direction of FIG. 1, typically may be in the range of 20 mm to 100 mm.

The exterior aircraft lighting device 2 is further equipped with an electronic control and evaluation unit 14, electrically connected to the light source 4 and the photo detector 8. The control and evaluation unit 14 is configured for controlling the light emitting elements 16 of the light source 4 and in particular for evaluating the state of wear of the light emitting elements 16 providing NEOL-detection based on the amount of reflected light detected by the photo detector 8.

For evaluating the state of wear of the light emitting elements 16, the control and evaluation unit 14 successively activates each of the light emitting elements 16 individually and evaluates the amount of light, which is reflected by the light entry side 6a of the optical element 6 and detected by the photo detector 8. The control and evaluation unit 14 in particular may comprise a memory unit 15 which is configured for storing at least one reference value. In this case, the state of wear of each of the light emitting elements 16 can be determined in particular by comparing the detection signal provided by the photo detector 8 with the at least one reference value.

In particular, different reference values may be provided for each of the light emitting elements 16 in order to take into account the different reflection angles depending on the respective position and/or different characteristics, in particular different colors of the light emitting elements 16.

The at least one reference value may be generated and stored in an initial initialization phase: After at least one new light emitting element 16 has been installed, each newly installed light emitting element 16 is individually activated and the resulting detection signal, which is provided by the photo detector 8, is stored as a reference value for the respective light emitting element 16.

In case the actual detection signal provided by the photo detector 8 is less than a certain portion, e.g. less than 70%, of the stored reference value, a notification signal may be triggered in order to indicate the need for replacement of the respective light emitting element(s) 16. Alternatively or additionally the respective light emitting element(s) 16 may be operated differently, in particular with an increased supply current, in order to compensate for the reduced light emission.

The exterior aircraft lighting device further comprises an indicator element 30, in particular an optical indicator element 30, which is configured for indicating a need for replacement of at least one of the respective light emitting element(s) 16.

In the exemplary embodiment shown in FIG. 1, the at least one indicator element 30 is visible from outside the aircraft when the exterior aircraft lighting device 2 is installed at an aircraft, allowing the pilot as well as service and maintenance personnel to determine the state of the cover easily in the course of outside inspection of the aircraft. Alternatively or additionally, the indicator element may be provided within the aircraft's cockpit for allowing a visual inspection by the cockpit crew.

As the amount of light emitted by the light emitting elements 16 may depend on the actual temperature, the temperature within the exterior aircraft lighting device 2 is detected by a temperature sensor 20 provided at the structural wall 22, and the temperature, at which the reference value(s) has/have been determined, is stored as a temperature reference value, as well.

In order to avoid false detection results, NEOL-detection is performed only when the actual temperature measured by the temperature sensor 20 is within a predetermined range around the stored temperature reference value.

Alternatively or additionally, different reference values may be stored for different temperatures/temperature ranges, and/or the reference value(s) and/or the actually measured detection signal(s) may be adjusted based on the difference between the actual temperature measured by the temperature sensor 20 and the previously stored temperature reference value in order to allow for correct NEOL-detection over a wide range of temperatures.

In order to detect color shifts, which might be caused by a degradation of the light emitting elements 16, "Fresnel reflections" from the light emitting elements 16 at the light entry side 6a of the optical element 6 may be measured for color coordinates. An additional colorful light emitting element 17, which in particular may be located in the vicinity of the main light emitting elements 16, can be activated to correct for chromatic shifts of the light output, in order to cause the total light emission to stay within a specified color window without replacement of any of the light emitting elements 16.

The state of wear of the light emitting elements 16 of the at least one light source 4 may be evaluated every time the exterior aircraft lighting device 2 is activated. Alternatively, the state of wear of the light emitting elements 16 of the light source 4 may be evaluated after a predetermined number of activations and/or after a predetermined period of time and/or operational time.

Figure 2:
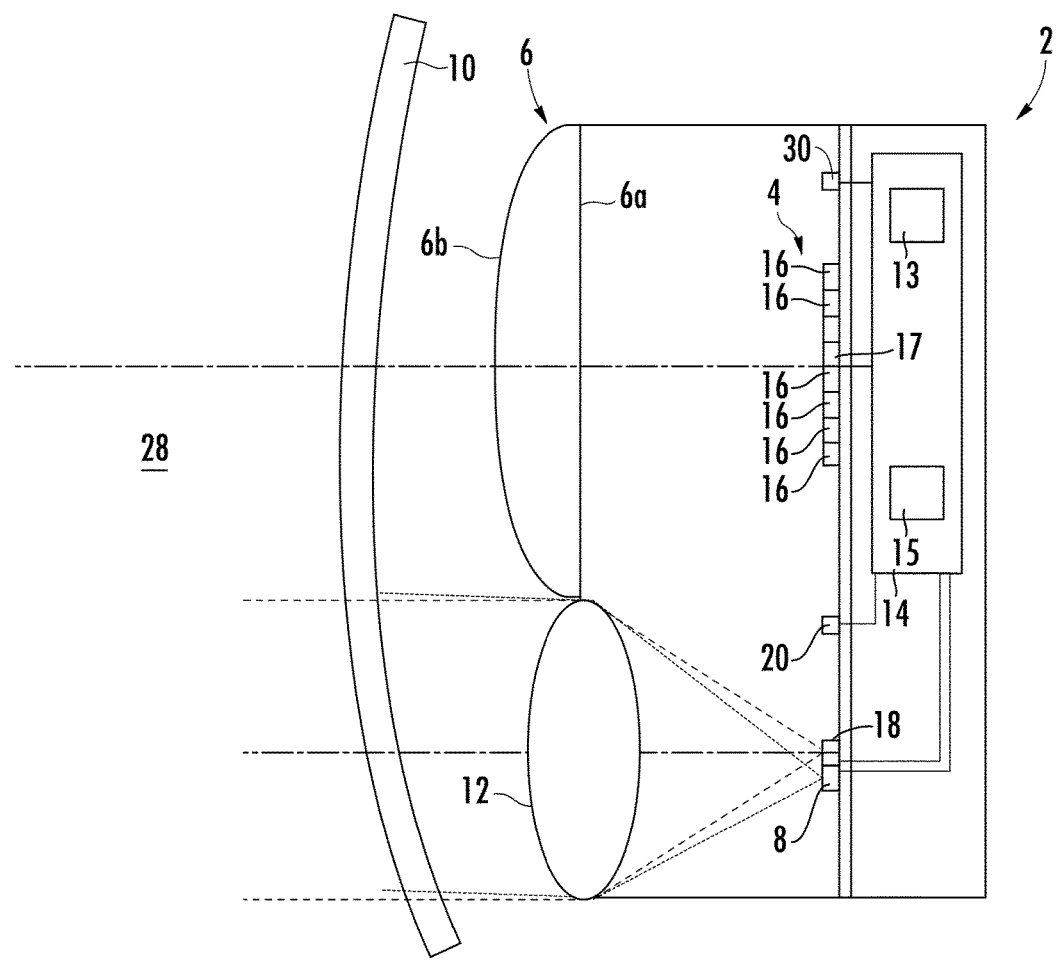
FIG. 2 shows a schematic cross-sectional view of an exterior aircraft lighting device according to a further exemplary embodiment of the invention.

FIG. 2 shows a schematic cross-sectional view of an exterior aircraft lighting device 2, according to another exemplary embodiment of the invention. The elements of said embodiment, which are identical with the elements of the embodiment shown in FIG. 1, are denoted with the same reference signs and will not be discussed in detail again.

The exterior aircraft lighting device 2 according to the exemplary embodiment illustrated in FIG. 2 additionally allows for detecting the state of erosion of the transparent external cover 10.

In the embodiment shown in FIG. 2, a reference light source 18 is provided at the structural wall 22 next to the photo detector 8, and an additional optical element 12 is located next to the optical element 6 between the structural wall 22 and the transparent external cover 10. Said additional optical element 12 is a lens, configured for focusing the light emitted by the additional reference light source 18 onto the external cover 10 and/or for focusing light, which has been reflected by the transparent external cover 10, onto the photo detector 8.

When new, the transparent external cover 10 reflects only a very small amount of light and most of the light is transmitted via the transparent external cover 10 of the lighting device 2 to the exterior space 28, shown on the left side of FIG. 2.

However, during the service life of the transparent external cover 10, its transmission properties deteriorate due to erosion, and in consequence, an increasing amount of light is reflected by the external cover 10. By comparing the actual detection signal provided by the photo detector 8 with a reference value, which has been determined and stored when the transparent cover 10 has been new, the amount of erosion may be determined. A signal indicating erosion of the transparent external cover 10 and need for replacement of the transparent external cover 10 may be triggered as soon as the difference between said actual value and the reference value exceeds a predetermined limit.

The photo detector 8 used for erosion detection of the transparent external cover 10 may be the same photo detector 8 as used for the detection of wear of the at least one light emitting element 16 of the light source 4. Alternatively, an additional photo detector, which is not shown in the Figures, may be used for detecting the erosion of the transparent external cover 10.

In a further embodiment, the control and evaluation unit 14 also comprises a counter 13, which is configured for counting the signals indicating erosion of the transparent external cover 10 ("erosion signals"), and a signal indicating the need for replacement of the transparent external cover 10 ("replacement signal") is triggered only after the number of erosion signals, in particular consecutive erosion signals counted by the counter 13, exceeds a predetermined value. By indicating an erosion of the at least partially transparent cover 10 only when the number of erosion signals, in particular the number of consecutive erosion signals counted by the counter 13, exceeds a predetermined value, the risk of issuing false replacement signals caused by a temporary soiling of the cover or a temporary dirt build-up on the external cover 10, deteriorating the cover's transmission properties, is minimized.

In said second exemplary embodiment, the exterior aircraft lighting device 2 thus does not only allow for an automatic NEOL-detection of the light source 4 and/or its light emitting elements 16, but also for automatically determining the amount of erosion of the transparent external cover 10. This allows a considerable reduction of the costs for maintenance without reducing safety.

While the invention has been described with reference to exemplary embodiments, it will be understood by those skilled in the art that various changes may be made and equivalents may be substituted for elements thereof without departing from the scope of the invention. In addition many modifications may be made to adopt a particular situation or material to the teachings of the invention without departing from the essential scope thereof. Therefore, it is intended that the invention not be limited to the particular embodiment disclosed, but that the invention include all embodiments falling within the scope of the following claims.

The invention claimed is:

1. An exterior aircraft lighting device comprising:
   at least one light source;
   an optical element configured for modifying light emitted by the at least one light source and having a light entry side and a light exit side;
   at least one photo detector configured and arranged for detecting a portion of the light emitted by the at least one light source, which is reflected by the light entry side of the at least one optical element, the photo detector providing at least one detection value representing the amount of detected light; and
   a control and evaluation unit configured for evaluating the state of wear of the at least one light source based on the at least one detection value provided by the at least one photo detector.

2. An exterior aircraft lighting device of claim 1, wherein the at least one light source comprises a plurality of light emitting elements, in particular a row or an array of LEDs.

3. An exterior aircraft lighting device of claim 2, wherein the control and evaluation unit is configured for successively activating and evaluating the plurality of light emitting elements.

4. An exterior aircraft lighting device of claim 1, wherein the control and evaluation unit is configured for comparing the at least one detection value provided by the at least one photo detector with at least one predetermined reference value.

5. An exterior aircraft lighting device of claim 1, further comprising a temperature sensor which is configured for measuring the temperature within the exterior aircraft lighting device and for providing a temperature value, and wherein the control and evaluation unit is configured for taking the temperature value into account when evaluating the state of wear of the at least one light source.

6. An exterior aircraft lighting device of claim 1, further comprising at least one colorful light emitting element which is operable to compensate for chromatic shifts of the light emitted by the at least one light source.

7. An exterior aircraft lighting device of claim 1, further comprising:
an external cover, and
a reference light source;
wherein the control and evaluation unit is configured for determining the state of erosion of the external cover by:
operating the reference light source for irradiating light onto the external cover;
detecting the amount of light, emitted by the reference light source and reflected by the external cover, by the at least one photo detector; and
evaluating the state of erosion of the external cover based on the amount of light detected by the at least one photo detector.

8. An exterior aircraft lighting device of claim 7, further comprising an additional optical element, which is arranged between the external cover and at least one of the photo detector and the reference light source, the additional optical element in particular being configured for focusing the light emitted by the additional reference light source onto the external cover and/or for focusing the light reflected by the external cover onto the at least one photo detector.

9. A method of evaluating the state of wear of at least one light source of an exterior aircraft lighting device, comprising the steps of:
operating the at least one light source for irradiating light onto a light entry side of at least one optical element, which is configured for focussing light, which has entered through the light entry side, and for emitting the focused light through a light exit side;
detecting a portion of light emitted by the at least one light source, which has been reflected by the light entry side of at least one optical element;
providing a detection value representing the amount of detected light; and
evaluating the state of wear of the at least one light source based on the provided detection value.

10. The method of claim 9, wherein the step of evaluating the state of wear of the at least one light source comprises the step of comparing the detection value with at least one predetermined reference value.

11. The method of claim 9, further including the steps of:
measuring the temperature within the exterior aircraft lighting device; and
taking the measured temperature value into account when evaluating the state of wear of the at least one light source.

12. The method of claim 11, wherein the method includes evaluating the state of wear of the at least one light source only when the measured temperature value is within a predetermined temperature range and/or adjusting the detection value and/or the reference value based on the measured temperature value.

13. The method of claim 9, wherein the exterior aircraft lighting device comprises a plurality of light sources, and wherein the method includes successively activating and evaluating each of the plurality of light sources.

14. The method of claim 9, further including the steps of operating an additional reference light source, irradiating light onto an external cover of the exterior aircraft lighting device; detecting an amount of light which is reflected by the external cover; and evaluating the state of erosion of the external cover based on the amount of light detected by the at least one photo detector.

15. The method of claim 14 further comprising the step of focusing the light emitted by the additional reference light source onto the external cover and/or focusing the light, which has been reflected by the transparent external cover onto the photo detector.

* * * * *